(12) United States Patent
Salcedo et al.

(10) Patent No.: US 8,110,202 B2
(45) Date of Patent: Feb. 7, 2012

(54) SYNTHETIC VACCINE FOR TICK CONTROL

(75) Inventors: Joaquim Homan Patarroyo Salcedo, Minas Gerals (BR); Marlene Isabel Vargas Viloria, Minas Gerals (BR); Aline Alencar Prates, Minas Gerals (BR); Marcio Alberto Mendes, Minas Gerals (BR); Fanny Guzman, Santa Fé de Bogotá (CO); Ricardo Wagner Dias Portela, Minas Gerals (BR); Ricardo de Castro Oliveira, Minas Gerals (BR); Manuel Elkin Murillo, Santa Fé de Bogotá (CO)

(73) Assignees: Universidade Federal de Viçosa, Viçosa (MG); Fundação de Amparo à Pesquisa do Estado de Minas Gerais, Belo Horizonte (MG)

( * ) Notice: Subject to any disclaimer, the term of this patent is extended or adjusted under 35 U.S.C. 154(b) by 0 days.

(21) Appl. No.: 11/190,816

(22) Filed: Jul. 28, 2005

(65) Prior Publication Data

US 2005/0281836 A1 Dec. 22, 2005

Related U.S. Application Data

(63) Continuation of application No. 10/275,304, filed as application No. PCT/BR01/00057 on May 4, 2001, now abandoned.

(30) Foreign Application Priority Data

May 4, 2000 (BR) ...................................... 0001717

(51) Int. Cl.
*A61K 39/00* (2006.01)
*A61K 38/00* (2006.01)

(52) U.S. Cl. .................. 424/265.1; 424/184.1; 530/300; 530/324

(58) Field of Classification Search .................. None
See application file for complete search history.

(56) References Cited

FOREIGN PATENT DOCUMENTS

| WO | WO 95/11998 | * | 5/1995 |
|----|-------------|---|--------|
| ZA | 9302352 A   |   | 8/1994 |

OTHER PUBLICATIONS

Rand et al (Proc. Natl. Acad Sci. Dec. 1989, vol. 86, p. 9657-9661).*
Rodriguez et al (Journal of Biotechnology, 33 (1994), 135-146).*
Rand et al; "Cloning and Expression of a Protective Antigen From the Cattle Tick *Boophilus microplus*"; Proc Natl Acad Sci USA, Dec. 1989, vol. 86, No. 24, pp. 9657-9661.
De La Fuente et al; "Vaccination Against Ticks (*Boophilus* Spp.): The Experience With the Bm86-Based Vaccine GAVAC"; Genet Anal, Nov. 1999, vol. 15 (3-5), pp. 143-148.

\* cited by examiner

*Primary Examiner* — Vanessa L. Ford
(74) *Attorney, Agent, or Firm* — Banner & Witcoff, Ltd.

(57) ABSTRACT

This invention is related to the field of immunology of protein biotechnology and particularly to the construction of synthetic immunogens which result, where inoculated, in the production by cattle of an immune response capable of lesion to the ticks feeding on the inoculated bovines, reducing their number, their weight and their reproductive capacity to such an extent that the constructed immunogen can be used as an effective vaccine for tick control on bovines. The technical object of the invention consists of the design and construction of two synthetic immunogens constituted of a continuous and defined sequence with forty-three (43) amino acids, found in different positions in the sequence of protein Bm86, their polymerization with cysteine in the N-terminal and in the C-terminal, the medicamentous composition based on said peptide(s) and the synthetic vaccine obtained thereby.

2 Claims, 2 Drawing Sheets

Kinetics of antibodies in animals made immune by peptide SBm4912. Arrows indicate inoculations and star indicates the time of challenge with *Boophilus microplus* larvae. T bars indicate the difference by addition of two standard deviations.

Kinetics of antibodies in animals made immune by SBm7462 peptide. Arrows indicate inoculations and star indicates the time of challenge with *Boophilus microplus* larvae. T bars indicate the difference by addition of two standard deviations.

FIGURE 2

SYNTHETIC VACCINE FOR TICK CONTROL

The present application is a continuation of U.S. application Ser. No. 10/275,304 filed May 12, 2003, now abandoned which is a 371 U.S. National Phase of International Application PCT/BR01/00057, filed May 4, 2001, which claims benefit of PI 0001717-5, filed May 4, 2000, the entire contents of each of which is hereby incorporated by reference.

FIELD OF THE INVENTION

This invention is closely related to the fields of protein biotechnology, immunology and particularly with the construction of synthetic immunogens which result, when inoculated in cattle, in the production by cattle of an immune response capable of lesion to the ticks feeding on the inoculated bovines, reducing the number of bovines, their weight and capacity of reproduction to such an extent that the constructed immunogen can be used as an effective vaccine for tick control in bovines.

BACKGROUND OF THE INVENTION

The tick *Boophilus microplus* (Canestrini, 1887), belonging to the Ixodoidae family, is the main bovine ectoparasite in Brazil and in all tropical and subtropical countries. This parasite is extremely well adapted to the climate of a large part of the country and, coupled with the presence of its hosts distributed over more than 80% of the nation's territory, constitutes a major problem to cattle raising in Brazil. The associated losses are not limited to the drop in production resulting from the intense hemophagia, but can also be related to other damages such as the inoculation of toxins from the salivary glands, depreciation of the hides, influencing the productive capacity of the animals and, chiefly, the transmission of various microorganisms that cause diseases which seriously affect cattle raising in the nation, such as *Babesia bovis* and *Babesa bigemina*, with participation also in the epidemiology of *Anaplasma marginale*.

The damage to livestock caused by ticks manifests itself by various typical actions, such as direct damage by the intense hematophagia originating mainly from the female ticks, and which can be as much as 0.6 to 3 ml per adult female. This results basically in loss of production, and various trials have been conducted to assess this situation. In 1987 (HOLROYD et al., *Australian Journal of Experimental Agriculture* 28: 1:10) observed that animals which had not been touched by ticks had gained on average 17 kg over a period of three years, as compared to those animals exposed to the parasite. In Brazil, (BRANCO et al 1987, *Coletânea de Pesquisas EMBRAPA/CNPO*, p. 229-234), found an average weight gain of 34.5 kg in Hereford cattle. In the country, FURLONG 1996 observed a reduced milk production in successive increasing infestations. JONSSON et al (*Veterinary Parasitology* 78: 66-77, 1998) have estimated that each adult female would be responsible for a drop of 8.9 ml in daily milk production and 1.0 g in loss of weight.

The loss caused by the tick bite and the consequent local inflammation adversely affect the value of the hide, which is of great concern in traditional areas of leather production.

The inoculation of toxins when sucking the blood, natural components of the tick saliva such as prostaglandin inhibitors and other modulators of the inflammatory response, which can lead to a hypersensibility reaction, paralysis of the members and even to testicular hypotrophy.

As to the transmission of pathogenic agents, the important ones in Brazil are the protozoa *Babesia bovis* and *Babesia bigemina*, with participation also in the epidemiology of *Anaplasma marginale* (PATARROYO, 1994, *Revista de Patologia Tropical* 23:145-146).

One must also include as losses to Brazilian livestock industry the costs of direct control of ticks and of the diseases for which they are carriers. HORN and ATECHE 1985 (*A Hora Veterinária* 4:12-32) have estimated the direct and indirect losses at 800 million dollars. The Ministry of Agriculture, in a paper covering the two years 1983/1984, raises that amount to one billion dollars per year, of which 40% represent losses in milk production. A paper by HORN in 1988 (Programa nacional de controle de parasitoses, in *Curso de Parasitologia Animal* 2:21-42) mentions expenditures of US$ 13,800,000.00 with acaricides, which would represent 15% of the nation's total cost of protection.

A number of approaches are used at present for tick control and the treatment of bovines with acaricides, which are chemical substances that kill the ticks. This methodology of control is disadvantageous in that a resistance is built against the chemicals in various tick populations, which necessarily leads to the introduction of new chemical substances for the control; the frequency of chemical treatments in an attempt at effective control of ticks in cattle herds; the harm that such chemical substances can cause to animals, the human health and the environment. Another alternative are the crosses of *Bos taurus taurus* and *Bos taurus indicus*, but these hybrids have a lower productive capacity than pure breeds, specifically in the case of dairy cattle, the use of chemical substances being necessary for the control stopping short of building tick resistance in such crossings. Still another proposed alternative for control is the use of pastures which would function in the non-parasitic phase of the parasite. Pasture rotation is also seen as an option since, depending on the resting time of each portion of the pasture, the born larvae would consume their food reserves and die before installing themselves in a host. The use of natural tick predators such as long-legged birds and birds of prey has also been researched, but the biologic and food chain risks of introducing such animals are not yet known. The ant *Pheidole megacephala* has been the subject of research as an alternative of less ecological impact. Natural parasites such as some bacteries and fungi of the species *Beauvenia bassiana* and *Metarhizium anisopliae* have also been analyzed. Another attempt at control has been the use of interspecific crossings of tick species to generate infertile males, but the frequency of intraspecific crossings exceeded that of interspecific crossings. All of the systems mentioned have problems of a practical nature, from the economic and/or ecological standpoints, which prevents their use in most of the geographical cattle raising areas.

In contrast to the foregoing description, the possibility of use of an effective vaccine for tick control constitutes an attractive alternative as compared to the methods available and in use at present.

Various attempts have been made to obtain immunization against the infestation of ticks in bovines. For the purpose of identifying the proteinaceous component and the organ in which the protective immunogenic factor would be found, larvae extracts, nervous tissue, hemocytes, hemolymph, genital tract, and eggs of *Boophilus microplus* were used, but these attempts were unsuccessful (DAVIDSON, S. 1985, Rural Research 128: 4-8; OPDEBEECK et al., 1988, Immunology 63: 363-367).

In 1989, (WILLADSEN et al., *Journal of Immunology* 143: 1346-1351) finally isolated and purified a protein which mimicked the alterations found with the gross tick extracts. That glycoprotein was designated Bm86, with an estimated weight of 89 kDa and a pI of 5.5. Subsequently, the amino acid sequence of this protein was determined, and it was found that the sequence was composed of 650 amino acids, of which 10% were cystein, showing a great analogy with the growth factor of the human epidermis (RAND et al, 1989, *Proceedings of the National Academic Sciences USA* 86:9657-9661).

By means of immunohistochemical techniques and monoclonal panels, the location and distribution of Bm86 in the tick's intestine were determined, and were found in the microvillosities of the membrane of the intestine epithelial cells and highly concentrated near the basal membrane (GOUGH and KEMP, 1933, *Journal of Parasitology* 79:900-907; LEE and OPDEBEECK, 1994, *International Journal of Parasitology* 25: 241-248).

Trials of vaccination with this protein reportedly show that the antibodies produced in bovines against the protein, as well as those generated by the inoculation of tick intestine extracts, are aggressive to the intestinal epithelium of the parasite, causing irreparable damage which will later affect the biological cycle of this ectoparasite.

Genetic studies which propitiated large-scale production of the protein through DNA cloning which encodes the Bm86 as *Escherichia coli* (TELLAM et al, 1992, *Animal Parasite Control Using Biotechnology*: 303-331), as *Aspergilus nidulans* and as Baculovirus (TURNBULL et al, 1990, *Applied Environmental Microbiology* 56: 2847-2852; TELAMM et al. 1992), have been performed, as well as vaccination trials, with up to 70% protection in some cases, resulting in a decrease of tick growth and affecting its biological cycle. Then, in 1994 the first vaccine against tick, named TICK-GARD® was commercially launched, through genetic engineering techniques in *E. coli* (SMITH et al, 1995).

In 1994 the second commercial vaccine against *Boophilus Microplus* was launched under the trade name GAVAC®, it was developed by Cuban research groups who expressed Bm86 in the yeast *Pichia pastoris* (RODRIGUEZ et al, *Journal of Biotechnology* 33: 135-146, 1994).

The third vaccine would come in 1996, the TICKGARD PLUS®, which has been successfully tested in various bovine breeds (WILLADSEN et al, *Veterinary Parasitology* 71: 209-222. 1997).

Notwithstanding the foregoing description, where it is shown that the use of commercial immunogens can result in significant reduction of infestation, they do not yet offer levels of protection which would make the use of conventional acaricides.

The purification procedures and obtention of immunogens for ticks in natura require an extremely ample and complex procedure. On the other hand, obtaining recombinant proteins requires the inconvenient preparation and handling of extensive cell cultures, either the fermentation or others intended for getting the proteinaceous material necessary for mass immunization, which is costly and may involve highly complex technical problems.

Obtaining new immunogens which can function as alternatives and/or complements to those already described represents a considerable advance in the development of effective vaccines.

In this context, we can note the propensity for new research, prompted by the recent progress of the knowledge in the areas of immunology, biochemistry, cell biology and biotechnology, for control of these parasites by vaccination.

Taking into account the fact that a protein can have several epitopes in its structure, which can act as protecting factors or not, and which can even be a mechanism of parasite mimicking to evade the immune response, it would be greatly advantageous to utilize vaccines having determinate and characterized epitopes, since this would avoid some problems brought about by the epitopes which are not necessary for developing protection and immunity against the parasite, such as suppressing, allergic and/or self-immune mechanisms, and typical evasion mechanisms of microorganisms.

Thus, a tick control vaccine based on the chemical synthesis of an immunogen would be more advantageous than a recombinant vaccine, such as high purity, because it does not require costly and complex purification techniques, its complete chemical characterization, it is safe because of the absence of contaminants, complete large-scale reproducibility, high stability, since it does not contain enzymes and other proteinaceous materials derived from other biologic materials, making its storage easier, and lower cost of production on an industrial scale.

SUMMARY OF THE INVENTION

The novelty of the present invention consists of the design and construction of two synthetic immunogens constituted of a continuous and defined sequence of forty-three (43) amino acids found in different positions in the protein Bm86 sequence, their polymerization with cysteines in the N-terminal and the C-terminal, the medicamentous composition based on said synthetic polypeptide(s) and the vaccine obtained thereby.

Therefore, the object of the present invention is constituted of the continuous and definitive of the forty-three amino acids, the manner of their polymerization using cysteine in their terminals, their medicamentous composition, thereby constituting the synthetic immunogen which can be advantageously used in the control by immunoprophylaxis of the bovine *Boophilus microplus* tick.

BRIEF DESCRIPTION OF THE DRAWINGS

FIG. 2 shows kinetics of antibodies in animals made immune by SBm7462 peptide.

DETAILED DESCRIPTION OF THE BEST MODE OF THE INVENTION

Figure 1:
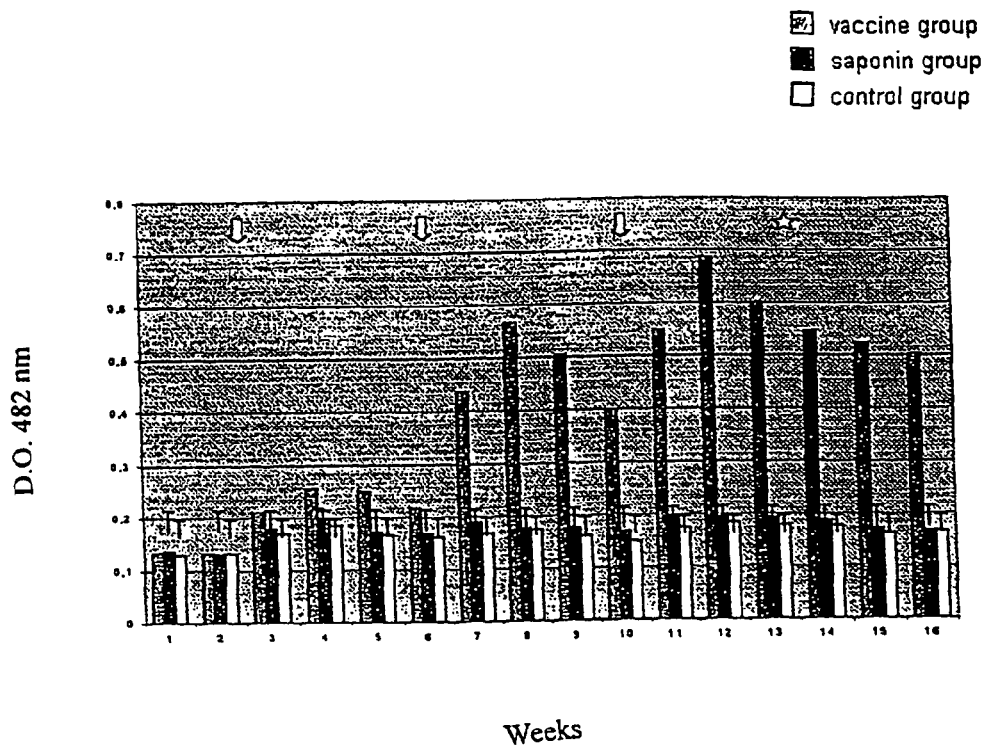
FIG. 1 shows the kinetics of antibodies in animals made immune by peptide SBm4912.

The peptides were formed having in view the structure of the Bm86 protein. The choice of these peptides within the structure of the integrate protein has been based on studies of computer prediction of immunogenic sites based on the protein properties, such as being antigenetic (HOOP and WOODS, 1981, Proceedings of the *National Academy of Science*, U.S.A. 78:3824-3828), potential of alpha and beta helixes and Beta Sheet (CHOU and FASMAN, 1978, *Advances of Enzymology of Relative Areas in Molecular Biology* 47:45-148), hydrophobicity and hydrophilic properties (KYTE and DOOLITTLE, 1982, *Journal of Molecular Biology* 157:105-132).

The synthesis was made in accordance with a known technique as described in (MERRIFIELD 1963, *Journal of the American Chemistry Society* 85: 2149). The methodology employed was the *Good Manufacture Procedure* (GMP), where a solid support is employed, in our case resin MBH4 (4-methylbenzidrilamine) with a substitution coefficient of 0.49 meq/g, weighed in accordance with the amount of peptides to be synthesized and amino acids protected in their side chains by the t-boc group (terbutylcarbonyl). The resin was placed in a polyethylene bag which was heat-sealed. A solution of 100 ml of diisopropylethylamine (DIEA) 5% in dicyclohexylcarbodiimide (DCC) was added to activate the resin.

The bag was dried and a solution of the first amino acid dissolved in dichloromethane (DCM) solvent or a solution of dimethylformamide (DMF) plus the DCC activator were added, with the amount of amino acid depending on its molecular weight and on the amount and type of the resin employed. These were incubated and stirred for one hour at room temperature. After this incubation, the bag of synthetic material was taken out, one of its ends was cut and a small portion of the resin was removed to check the full coupling of the amino acid to the resin, by the ninhydrin test. With the positive test, the coupling was repeated using 1-hydroxybenzotriazole (HOBT) hydrate. With the negative test, the synthesis continued, by the addition of 100 ml of trifluoroacetic acid (TFA) in DCM to withdraw the protection of amino groups, washing with DCM and isopropanol and incubation with the next amino acid of the peptide sequence. At the end of the synthesis, the material was subjected to cleavages for removal of the t-boc groups and the resin, and to HPLC chromatography to determine the level of efficiency and purity of the synthesis, subsequently lyophilized and then stored in eppendorf tubes containing 40 mg at the temperature of $-20°$ C.

In order to test the capacity of the peptides in inducing a protective immune response, Bos taurus taurus calves 8 to 10 months old were inoculated. These animals were kept in isolation, free from the infestation of ticks, flies and other ectoparasites. These animals were separated into four groups, with four animals in each group.

Group 1—Control, which was inoculated with 4 ml of sterile water milliQ, via subcutaneous, in three (3) doses, the first one on day zero (0), the second one on day 30 and the third one on day 60.

Group 2—Saponin, inoculated with 1.5 mg of saponin adjuvant diluted in 4 ml of sterile water milliQ, administered via subcutaneous on the same dates of inoculation of the Control group.

Group 3—Inoculated with the synthetic peptide named SBm4912 (Synthetic Boophilus microplus 4912), in a solution of 2.0 mg of synthetic peptide and 1.5 mg of saponin adjuvant, diluted in 4 ml of sterile water milliQ, administered via subcutaneous, following the same time schedule established for the other groups.

Group 4—Inoculated with the synthetic peptide named SBm7462 (Synthetic Boophilus microplus 7462), inoculated with 4 ml of a solution containing 1.5 mg of saponin adjuvant and 2.0 mg of synthetic peptide diluted in sterile water milliQ, administered via subcutaneous on the same dates as the preceding groups.

The animals were constantly monitored twice a day during five days following inoculation to check for possible reactions of cutaneous hypersensitivity to peptides and the adjuvant. To identify possible hemolytic effects of the peptides (CALVO et al, 1991, Peptides Research 4:324-333) in addition to daily visual inspection of the inoculation point, hematocrit tests were made in all the animals within five days following inoculation.

After 21 days from the last inoculation, the animals were challenged with larvae of Boophilus microplus amounting to 1500 larvae per day during three successive days, for a total of 4500 larvae per animal.

Clinical observations were made weekly until the eighteenth day and daily thereafter, to check the development and predict the probable day when shedding the adult females would start.

On the twenty-first day, when the females began to fall, a procedure was initiated to collect all adult females found on the floor of the bays, in the feeding trough and on the sewage disposal grate. For a more careful collection, the bay was washed twice a day and all of the material resulting from the washing was sifted and the adult females were removed and identified according to the bay from which they came and the inoculation group. The females were then individually packed and identified. Each female was weighed on a precision scale and left for egg laying during 15 days in a B.O.D. stove at 27° C. and 80% humidity (OBA, 1976, Revista da Faculdade de Veterinária e Zootecnia da Universidade de São Paulo, 13:409-420), at which time the eggs of each tick were weighed. These eggs were cut into 20 portions of 75 mg each (1500 eggs) per group and incubated for 30 days in a B.O.D. stove, with daily observation of the eclosion process. The larvae were then weighed on a precision scale (MASSARD et al, 1995, Revista Brasileira de Medicina Veterinária 17:167-173). To assess the effect of the synthetic immunogens on the biological parameters of the ticks, the formulae recommended by DE LA FUENTE for the rBM86 (Recombinant vaccines for the control of cattle tick, Habana: Elpos Scientiae, 280 p., 1995) were used for each vaccine group and for the control group and the control of the adjuvant, as shown below:

$$DT(\%)=100[1-(NTV/NTC)]$$

where:
DT(%) Percent reduction of number of adult females
NTV Number of adult females per each vaccine group
NTC Number of adult females in Control group $$DR(\%)=100[1-(PMTV/PMTC)]$$

where:
DR(%) Percent reduction of average adult females weight
PMTV Average weight of adult females for each vaccine group
PMTC Average weight of adult females in Control group $$DO(\%)=100[1-(PMOV/PMOC)]$$

where:
DO(%) Percent reduction of average egg weight
PMOV Average egg weight for each vaccine group
PMOC Average egg weight in Control group $$DF(\%)=100[1-PPLOV/PPLOC]$$

where:
DF(%) Reduction in the fertility of the eggs
PPLOV Average weight of larvae per gram of eggs in each vaccine group
PPLOC Average weight of larvae per gram of eggs in Control group $$EF(\%)=100[1-(CRT \times CRO \times CRF)]$$

where:
EF(%) Effectiveness of peptide used as a vaccine
CRT Reduction in the number of adult females
CRO Reduction in egg laying capacity
CRF Reduction in fertility In order to assess the kinetics of synthetic anti-peptide antibodies produced in the inoculated bovines, blood samples were taken. The collection of blood of the animals in this experiment observed the following schedule: two weekly collections before the first inoculation, four weekly collections after the first inoculation, four weekly collections after the second inoculation, and six weekly collections after the third inoculation. The serum obtained from each sample was aliquoted into eppendorf tubes at $-20°$ C. The kinetics was measured using the ELISA immunoenzymatic test.

The data on the biological parameters analyzed after counting and weighting the adult females, weighting eggs and larvae, are shown in Table 1, as well as the parameters of the reduction in number and weight of the adult females, the weight of the eggs, the fertility and the effectiveness.

It could be observed that the adult females loosened from the animals vaccinated with the synthetic peptides SBm4912 and SBn7462 had a lower weight and statistically different from the control and saporin groups, not significantly different among themselves. In the analysis of the average weight of the eggs, it was found that the results from groups 3 and 4 were significantly lower than those of the Control group, and statistically equal among themselves. In weighing the ratio larvae/gram of eggs, the picture obtained was similar to the preceding one.

In comparing the percentage factors of reduction in weight and number of adult females, of the weights of eggs and larvae, the conclusion is that the SBm4912 and SB7462 peptides obtained a significant level of reduction and effectiveness. The kinetics of anti-peptide antibodies (IgG) appears to be a typical IgG immune response produced by a non-synthetic antigen, these results are shown in FIGS. 1 and 2.

Peptides SBm4912 and SBm7462 did not cause when inoculated adverse reactions or discomfort to the inoculated animals.

Advantages of the Proposed Solution:

A vaccine for tick control based on the chemical synthesis of an immunogen offers advantages such as:

its high level of purity because it does not require expensive and complex purification techniques;

its full chemical characterization;

safety as to the absence of contaminants;

full reproducibility on a large scale;

high stability as it does contain enzymes and other proteinaceous materials from other biological materials, which makes its storage easier;

low cost of production on an industrial scale.

The following Table 1 shows the Biological parameters of *Boophilus microplus* from animals inoculated with the synthetic peptides and from the control group and the adjuvant control group. The letters (a, b, c) indicate significant statistical differences at the significance level of 0.01% in the Tukey Test.

TABLE 1

| Biological parameters | Groups | | | |
|---|---|---|---|---|
| | Control | Saponin | 4912 | 7462 |
| Average adult Females weight | $0.31586^a$ | $0.314124^a$ | $0.280386^b$ | $0.289074^b$ |
| Average egg-laying weight | $0.159087^a$ | $0.16805^a$ | $0.111706^b$ | $0.115292^b$ |
| Weight of larvae/gram of eggs | $0.857^a$ | $0.828^a$ | $0.617^b$ | $0.573^b$ |
| Weight reduction adult females (DR) | | | $8.328\%^a$ | $5.448\%^b$ |
| Weight reduction of eggs (DO) | | | $29.78\%^a$ | $27.53\%^b$ |
| Reduction of adult females (DT) | | | $45.39\%^a$ | $60.92\%^b$ |
| Reduction of fertility (DF) | | | $28.04\%^a$ | $33.12\%^a$ |
| Effectiveness (EF) | | | $72.4\%^a$ | $81.05\%^b$ |

The object of this invention is likely to be improved and modified, without disrupting the essence of the concept and scope of the invention, which is limited only by the scope of attached claims.

What is claimed is:

1. A synthetic vaccine against ticks comprising a polypeptide consisting of CLSKHVLRKLQACEHSSICSDFGNEFCRNACDCGEWGAMNMTTRC (SEQ ID NO: 1).

2. A composition comprising (1) a polypeptide consisting of CLSKHVLRKLQACEHSSICSDFGNEFCRNACDCGEWGAMNMTTRC (SEQ ID NO: 1); and (2) an adjuvant.

* * * * *

SEQUENCE LISTING

<160> NUMBER OF SEQ ID NOS: 2

<210> SEQ ID NO 1
<211> LENGTH: 45
<212> TYPE: PRT
<213> ORGANISM: Artificial Sequence
<220> FEATURE:
<223> OTHER INFORMATION: Description of Artificial Sequence: synthetic
      Boophilus microplus 4912

<400> SEQUENCE: 1

Cys Leu Ser Lys His Val Leu Arg Lys Leu Gln Ala Cys Glu His Ser
 1               5                  10                  15

Ser Ile Cys Ser Asp Phe Gly Asn Glu Phe Cys Arg Asn Ala Cys Asp
            20                  25                  30

Cys Gly Glu Trp Gly Ala Met Asn Met Thr Thr Arg Cys
        35                  40                  45

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: synthetic
      Boophilus microplus 7462

<400> SEQUENCE: 2

-continued

```
Cys Leu Ser Lys His Val Leu Arg Lys Leu Gln Ala Cys Glu His Cys
 1               5                  10                  15

Asp Cys Gly Glu Trp Gly Ala Met Asn Met Thr Thr Arg Ser Ser Ile
            20                  25                  30

Cys Ser Asp Phe Gly Asn Glu Phe Cys Arg Asn Ala Cys
            35                  40                  45
```